(12) United States Patent
Mackovic-Basic (10) Patent No.: US 12,108,955 B1
(45) Date of Patent: Oct. 8, 2024

(54) SURGICAL INSTRUMENT AND METHOD FOR OCCLUSION OF UTERINE BLOOD VESSELS

(71) Applicant: Miriam Mackovic-Basic, Austin, TX (US)

(72) Inventor: Miriam Mackovic-Basic, Austin, TX (US)

( * ) Notice: Subject to any disclaimer, the term of this patent is extended or adjusted under 35 U.S.C. 154(b) by 0 days.

(21) Appl. No.: 18/444,173

(22) Filed: Feb. 16, 2024

(51) Int. Cl.
*A61B 17/132* (2006.01)
*A61B 17/42* (2006.01)
*A61B 17/00* (2006.01)

(52) U.S. Cl.
CPC .......... *A61B 17/1322* (2013.01); *A61B 17/42* (2013.01); *A61B 2017/00862* (2013.01)

(58) Field of Classification Search
CPC . A61B 17/1322; A61B 17/42; A61B 17/4241; A61B 17/44; A61B 17/442; A61B 2017/00862; A61B 2017/12004; A61B 2017/12009; A61B 2017/4216
See application file for complete search history.

(56) References Cited

U.S. PATENT DOCUMENTS

| | | | | |
|---|---|---|---|---|
| 928,011 A * | 7/1909 | Whitlock | ....... | A61B 17/320708 606/160 |
| 3,326,217 A * | 6/1967 | Kerr | ............. | A61B 17/1227 606/158 |
| 3,667,471 A * | 6/1972 | Doty | ............ | A61B 17/12 24/280 |
| 3,810,456 A * | 5/1974 | Karman | ............. | A61F 6/142 128/830 |
| 5,383,882 A * | 1/1995 | Buess | ............. | A61B 17/12013 606/151 |
| 5,782,839 A * | 7/1998 | Hart | ............. | A61B 17/0218 606/198 |
| 8,465,496 B2 * | 6/2013 | Mackovic Basic | .... | A61B 17/42 606/119 |
| 8,968,344 B2 * | 3/2015 | Forsell | ............. | A61F 5/0066 606/151 |
| 9,445,839 B2 * | 9/2016 | DiBenedetto | ......... | A61B 17/44 |
| 10,010,345 B2 * | 7/2018 | Mackovic Basic | .... | A61B 17/12 |
| 10,058,333 B2 * | 8/2018 | Burleigh | ............. | A61B 17/128 |
| 11,259,790 B2 * | 3/2022 | Valenti | ............. | A61B 17/0218 |
| 11,364,032 B2 * | 6/2022 | Cabrera Aquino | ............. | A61B 17/12013 |

(Continued)

*Primary Examiner* — Ryan J. Severson
(74) *Attorney, Agent, or Firm* — Omni Legal Group; Omid E. Khalilch; Ariana K. Santoro (57) ABSTRACT

A surgical instrument for at least partial occlusion of uterine blood vessels during surgery involving the uterus and a method for using the same is provided. The surgical instrument comprises an elongated, flexible tourniquet having a first end and a second end. A lashing member is disposed at or proximate to the first end while a portion of the tourniquet proximate to the second end defines a series of successive holes configured to releasably and even adjustably maintain the lashing member in place so that the tourniquet may form a secure loop. The surgical instrument may further comprise an introducer formed as a flexible yet resilient sheath configured to aid placement of the tourniquet around a lower uterine segment and uterine vessels. In accordance with the method, once the tourniquet is placed and lashing member is secured, the sheath may be removed from the tourniquet, and operation may proceed.

19 Claims, 6 Drawing Sheets

(56) References Cited

U.S. PATENT DOCUMENTS

| | | | |
|---|---|---|---|
| 2006/0173486 A1* | 8/2006 | Burke | A61B 17/12099 606/193 |
| 2010/0234862 A1* | 9/2010 | Patel | A61B 17/12009 606/151 |
| 2011/0251622 A1* | 10/2011 | Basic | A61B 17/12 606/119 |
| 2012/0123450 A1* | 5/2012 | Forsell | A61F 5/0066 606/151 |
| 2014/0309671 A1* | 10/2014 | Basic | A61B 17/12 606/158 |
| 2014/0324073 A1* | 10/2014 | Junger | A61B 17/12013 606/157 |
| 2015/0066056 A1* | 3/2015 | Cabrera Aquino | A61B 17/12013 606/140 |
| 2016/0066917 A1* | 3/2016 | Burleigh | A61B 17/128 606/157 |
| 2016/0166283 A1* | 6/2016 | DiBenedetto | A61B 17/4241 606/119 |
| 2017/0000525 A9* | 1/2017 | Basic | A61B 17/28 |
| 2020/0229846 A1* | 7/2020 | Azpurua-Pardi | A61B 17/12013 |

\* cited by examiner

SURGICAL INSTRUMENT AND METHOD FOR OCCLUSION OF UTERINE BLOOD VESSELS

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to surgical instruments and more particularly to a tourniquet assembly for at least partial occlusion of uterine blood vessels used in performing cesarean sections and other surgical procedures of the uterus.

BACKGROUND

The United Nations estimates that about 385,000 babies are born each day around the world. Despite how common childbirth is, childbirth carries many risks, such as infection, mutilation, and even death. Indeed, one in five women will experience a life-threatening condition called post-partum hemorrhaging as a result of delivery. This condition is characterized by substantial blood loss. A committee opinion published by The American College of Obstetricians and Gynecologists noted that postpartum hemorrhage causes approximately 11% of maternal deaths in the United States and that between 54-93% of these may be preventable. The World Health Organization reports that post-partum hemorrhage results in about 70,000 maternal deaths globally each year. While post-partum hemorrhaging can occur during vaginal delivery, it is more common in women who deliver through cesarean section ("C-section"), which is an increasingly common surgical method for delivery.

One of the reasons that C-sections are more likely to result in post-partum hemorrhages is due to the length of time between making the initial incision in the patient's abdomen and the closing of the incisions. While delivering the baby is the primary concern following incision, this takes approximately five minutes, and the majority of the approximately hour-long operation is spent suturing the incisions to close the patient. One reason that this takes so long is that blood in the field needs to be cleared in order to suture the patient, which causes even more blood to be lost. Thus, there is a need to reduce blood flow to the surgical field during C-sections, which reduces the blood in the field that needs to be cleared, reduces the length of time it takes to conduct C-sections, and overall reduces the risk of post-partum hemorrhaging. All of this, in turn makes recovery easier for the mother.

Despite the fact that C-sections rank among the most common surgical procedures, equipment designed for the complex uterine anatomy is rare. Instead, many physicians utilize generic surgical instruments during C-sections, such as the hemostatic clamp proposed in U.S. Pat. No. 3,326,217 to Sydney. However, general surgical instruments are designed for use with larger areas of the body and, when used during a C-section, often come into contact with unintended areas.

Uterine anatomy is not only complex, but it is also cramped, with many important and delicate anatomical structures in close proximity to one another. As a result, using general surgical instrument in this area carries the risk of causing damage and potential fertility issues due to their ill-fitting nature. For example, when targeting the uterine vessels along the lower uterine segment, the size of the surgical instrument often results in unintended contact with the bladder. Additionally, general surgical instruments often utilize handles or arms to assist with placement, which may be disadvantageous given the intricacy of uterine anatomy. These handles or arms risk contacting unintended structures, make direct placement to a targeted structure challenging. Indeed, depending on the particular size and shape of the handles or arms, they may themselves even further crowd the surgical field. As a result, while general surgical instruments may be utilized at times, many physicians are reluctant to utilize these tools given their increased risk of complications.

This applies to other operations that require manipulation of the uterus while ensuring the preservation of its functional aspects and anatomical structures. For instance, uterine myomectomy refers to the surgical removal of uterine leiomyomas, or fibroids. In such procedures, access to the uterus is gained in much the same way as during a C-section, and thus, the risk of hemorrhage is present.

Applicant has herself previously proposed U.S. Pat. No. 10,010,345 for an improved surgical clamp used for the partial occlusion of uterine vessel, operative to reduce the blood flow in the lower uterine segment. Another device proposed to staunch postpartum hemorrhage in particular also appears in U.S. Pat. Pub. No. 2006/0173486 by Burke et al. One childbirth-specific instrument proposed to reduce blood loss during delivery is provided in U.S. Pat. No. 9,445,839 to DiBenedetto, which provides a uterine clamp comprising two plates that apply pressure to the uterus in an attempt to get the uterus to contract and reduce the blood flow following delivery. Still, these clamps are deficient as tools to reduce hemorrhage on their own, as their use is limited by anatomical positioning and even size of a patient's uterus. As a result, some have proposed occluding uterine vessels by the use of a temporary uterine tourniquet often made on an ad hoc basis out of rubber bands and even bladder catheters. In such cases, a length of surgically acceptable rubber or the like may be temporarily, manually tied or knotted and clamped around the lower uterine segment as an effective method for reducing the amount of perioperative bleeding in patients during C-sections and myomectomies. However, this impromptu approach to reducing blood flow has limitations. For instance, it can be challenging to position such a tourniquet within the surgical field and is also challenging to adjust and stabilize to achieve the desired level of occlusion.

Thus, there is a need for an improved device, such as a surgical instrument, that may be utilized to reduce blood loss during operations on the uterus.

SUMMARY

The present disclosure is directed to a surgical instrument for reducing blood loss during surgeries involving the uterus, such as cesarean sections, and methods thereof. More particularly, the surgical instrument may comprise a tourniquet and surgical introducer assembly operative to at least partially occlude uterine blood vessels during cesarean sections and other uterine surgical procedures.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, the device may be a surgical instrument comprising a tourniquet formed as an elongated, flexible, and resilient band, strip, tape, cord, belt, or the like configured to be selectively secured around patient anatomy to effect a desired level of occlusion. For the sake of brevity, a uterus and surrounding ligaments and uterine vessels will be referred to as exemplary patient anatomy, however, one of ordinary skill in the art will recognize that the surgical instrument may be applied to at least partially occlude blood flow in other areas of the body without departing from the invention. In addition, the uterine ligaments and uterine vessels may be referred to throughout as collective pluralities for the sake of brevity. However, it is to be understood that at any time, any number of such ligaments or vessels, or none at all, may be occluded by the tourniquet without departing from the invention. Therefore, in an exemplary embodiment, the tourniquet may be more or less tightly secured around the patient's uterus, one more uterine vessels, and/or if needed or desired, one or more uterine ligaments, to completely or partially occlude blood flow to a desired extent during operations on the uterus. To achieve this, the tourniquet may comprise a first end and a second end with a lashing member disposed at or near the first end. A portion of the tourniquet proximate to the second end may define a plurality of holes therethrough, sized to securely but releasably maintain the lashing member in position around the patient's uterus and uterine vessels.

In one embodiment, the lashing member may be a pin, prong, or the like. In some embodiments, the lashing member may be configured to engage with any of the plurality of holes more securely. For instance, the lashing member may be a prong, a bent prong, or even a pin with a head. The particular form taken by the lashing member will not limit the invention.

In some embodiments, the surgical instrument further comprises an introducer configured as a curved length of resilient material operative to guide the tourniquet into place around a patient's lower uterine segment and any surrounding vessels, ligaments, and other structures, as desired or needed. In practice, the introducer provides the flexible and resilient tourniquet with a pathway around tissue, ligaments, and/or vessels near a surgical site, which, in the exemplary embodiment, would be an incision in the uterus. More particularly, the introducer comprises a first end and a second end wherein the first end defines an open-ended sheath configured to receive the first end of the tourniquet.

The introducer may be resilient but also, to some extent, stiff, which avoids a need to handily manipulate delicate anatomical structures in order to lash the tourniquet around a targeted area. That is, the introducer may be generally resistant to deformation but is not completely inflexible. Indeed, this avoids a need to handily manipulate nearby but ultimately uninvolved structures as well. For instance, a patient's bladder may be positioned in front of or proximate to the patient's lower uterine segment. Thus application of a tourniquet around the lower uterine segment, uterine vessels, and/or uterine ligaments in the absence of an introducer may require potentially injurious manipulation of the bladder, ureters, and other anatomical structures. When deployed during a surgical procedure on the uterus, however, the first end of the introducer as well as the sheathed first end of the tourniquet may be threaded behind or along a back side of the lower segment of the uterus, uterine ligament(s), and/or uterine vessel(s)—avoiding disturbance of the bladder as needed. Then, from a front side of the lower segment of the uterus, the introducer may be slidably adjusted toward the second end of the tourniquet to permit insertion of the lashing member into one of the plurality of holes in order to form the tourniquet as a secure loop around the lower segment of the uterus, uterine ligaments, and/or uterine vessels. The introducer may be sliadably removed from the tourniquet once the tourniquet is secured as a loop around the lower segment of the uterus, uterine ligaments, and/or uterine vessels to the desired degree, or once the first end of the tourniquet is accessible from the front side of the lower segment of the uterus, as desired by a user.

The tourniquet may comprise a variety of biocompatible materials without departing from the invention. In some embodiments, for instance, the tourniquet may comprise compressible surgical foam and/or gel operative to selectably compress when removably secured around the lower uterine segment and vessels. In some embodiments, the tourniquet may comprise a plurality of layers. In such embodiments, one or more internal layers may comprise the compressible surgical foam and/or gel while an external layer comprises surgical cotton, drapes, or gauze known to those of ordinary skill in the art for beneficially frictionally but gently gripping tissue and even absorbing moisture.

Likewise, the introducer may comprise a variety of flexible, biocompatible materials without departing from the invention. For instance, the introducer may comprise polyvinylidene fluoride (PVFD), polyamide or nylon, polyethylene terephthalate (PET), or polycarbonate, among others known to those of ordinary skill in the art.

In some embodiments, the tourniquet has distinctly formed inside and outside. For instance, in some embodiments, the inside of the tourniquet will contact the uterus when applied to at least partially occlude uterine blood vessels, and the outside of the tourniquet will face outward from the uterus and at least partially occluded vessels. In such cases, it may be desirable to configure the tourniquet as an elongated and flexible band, strip, tape, cord, belt, or the like, having a flat inside and a rounded outside. It is contemplated that providing a flat inside may improve occlusion of the blood vessels. Still, it is possible that the tourniquet may be cross-sectionally round, elliptical or any other shape needed or desired without departing from the invention.

It is contemplated that surgical instruments, according to the disclosure and claims provided below, the surgical instrument may beneficially reduce blood loss and prevent or abate hemorrhage during C-sections and other uterine surgeries while avoiding potentially injurious manipulation of the uterus and surrounding anatomical structures.

Thus, it is an object of the invention to enable targeted and adjustable occlusion of blood flow during surgical procedures.

It is another object of the invention to reduce complications, including maternal and infant mortality, caused by blood loss during childbirth.

It is still another object of the invention to provide an adjustable tourniquet to reduce blood loss during surgical procedures.

It is yet a further object of the invention to provide a guide that aids placement of a tourniquet around the targeted anatomy in a crowded surgical field.

One or more of the above-disclosed embodiments, in addition to certain alternatives, are provided in further detail below with reference to the attached figures. The disclosed subject matter is not, however, limited to any particular embodiment disclosed.

The disclosed embodiments may be better understood by referring to the figures in the attached drawings, as provided below. The attached figures are provided as non-limiting examples for providing an enabling description of the method and system claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

Figure 1:
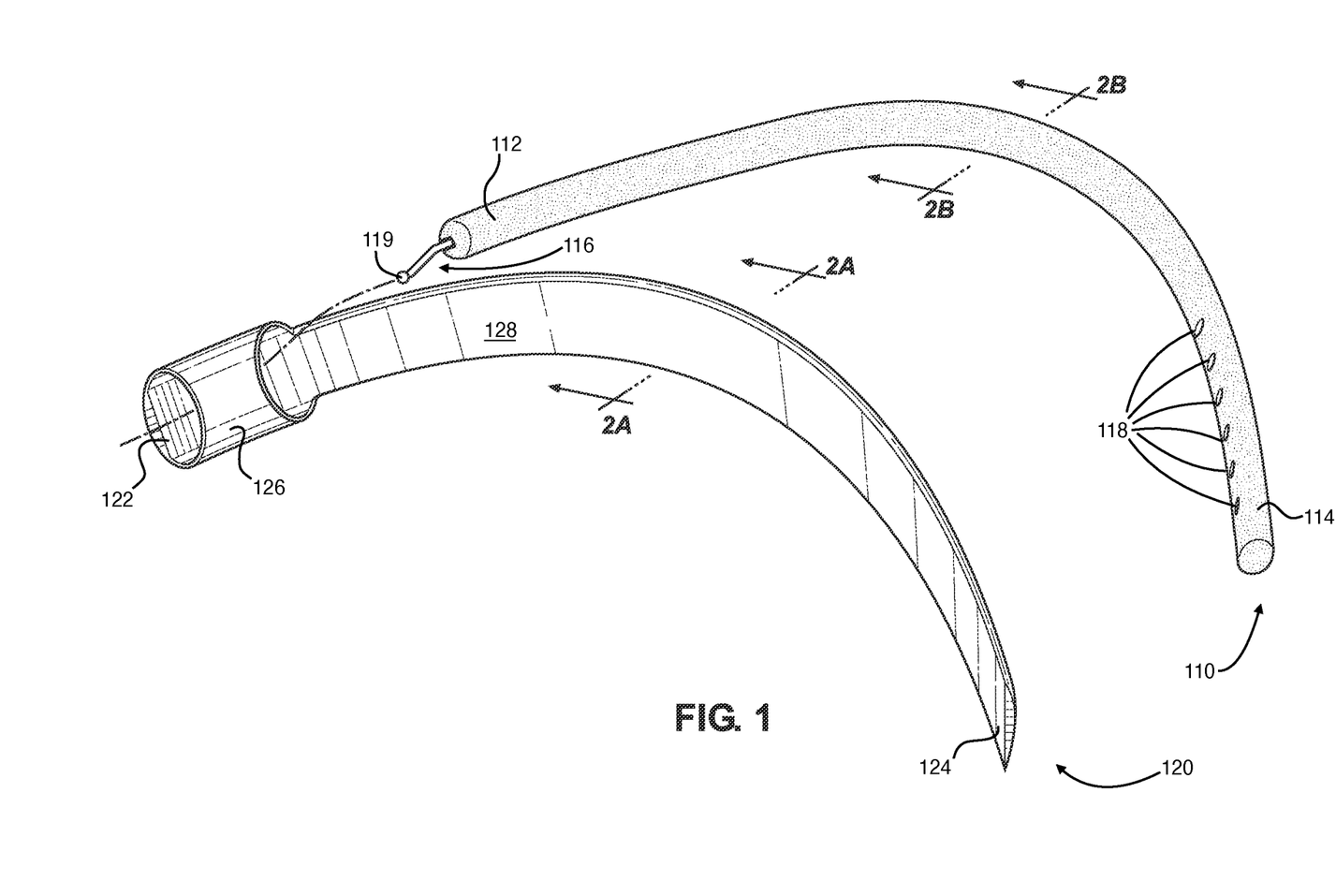
FIG. 1 shows an exploded, perspective view of one embodiment of a surgical instrument for occlusion of uterine blood vessels.

With reference to FIG. 1 a surgical instrument comprises a tourniquet 110 formed as an elongated, flexible, and resilient band, strip, tape, cord, belt, or the like configured to be selectively secured around patient anatomy to effect a desired level of occlusion. The tourniquet 110 may comprise a first end 112 and a second end 114 with a lashing member 116 disposed at or near the first end 112. A portion of the tourniquet 110 proximate to the second end 114 may define a plurality of holes 118 therethrough, sized to securely but releasably maintain the lashing member 116 in position around the patient's uterus and uterine vessels.

In one embodiment, the lashing member 116 may be a pin, prong, or the like, some embodiments, the lashing member 114 may be configured to engage with any of the plurality of holes 118 more securely. For instance, the lashing member 116 may be a prong, a bent prong, or even a pin with a head. In the depicted example, the lashing member 116 is a pin having a head 119 wider than the pin's body. In addition, the body of the pin is bent. It is contemplated that bending the lashing member 116 and providing a head 119 may prevent the lashing member 116 from undesirably or untimely disengaging from any of the plurality of holes 118, however, the particular form taken by the lashing member 116 will not limit the invention.

In some embodiments, the surgical instrument further comprises an introducer 120 configured as a curved length of resilient material having a first end 122 and second end 124, sized in length and width to accommodate the length and width of the tourniquet 110. In some embodiments, the first end 122 defines an open-ended sheath 126 configured to receive the first end 112 of the tourniquet 110 along lines 2A and 2B. The hollow cross-section of such sheath 126 is shown for reference in FIG. 2A.

Returning to FIG. 1, the introducer 120 may comprise a variety of flexible, biocompatible materials without departing from the invention. For instance, the introducer 120 may comprise polyvinylidene fluoride (PVFD), polyamide or nylon, polyethylene terephthalate (PET), or polycarbonate, among others known to those of ordinary skill in the art. As such, it will be seen that the introducer 120 may be resilient but also, to some extent, stiff, which avoids a need to handily manipulate delicate anatomical structures in order to lash the tourniquet 110 around a targeted area during use.

Likewise, it is contemplated that the tourniquet 110 may comprise a variety of biocompatible materials. In some embodiments, for instance, the tourniquet 110 may comprise compressible surgical foam and/or gel operative to selectably compress when removably secured around the lower uterine segment and vessels. In some embodiments, as in FIG. 2B, the tourniquet may comprise a plurality of layers. In such embodiments, one or more internal layers 132 may comprise the compressible surgical foam and/or gel while one or more external layers 134 comprises surgical cotton, drapes, or gauze selected for beneficially, frictionally but gently gripping tissue and even absorbing moisture.

While the exemplary tourniquet 110 is shown as symmetrically elliptical in FIG. 2B, it is contemplated that the tourniquet 110 may define a distinct inside and outside. For instance, in some embodiments, the inside of the tourniquet will contact the uterus when applied to at least partially occlude uterine blood vessels, and the outside of the tourniquet will face outward from the uterus and at least partially occluded vessels. In such cases, it may be desirable to configure the tourniquet as an elongated and flexible band, strip, tape, cord, belt, or the like, having a flat inside and a rounded outside rather than the symmetrically rounded sides of the exemplary tourniquet 110. It is contemplated that providing a flat inside may improve occlusion of the blood vessels. Still, it is possible that the tourniquet may be cross-sectionally round, elliptical or any other shape needed or desired without departing from the invention.

Figure 2A:
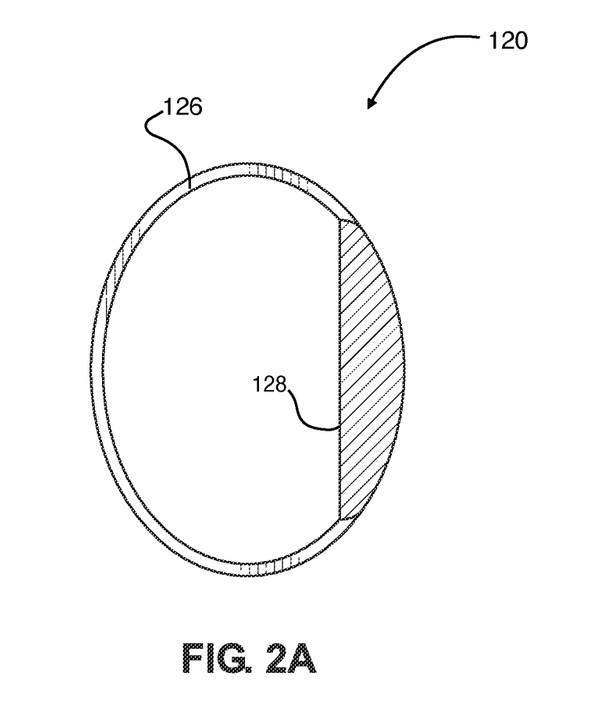
FIG. 2A shows a cross sectional view of an introducer as one aspect of the surgical instrument for occlusion of uterine blood vessels.
Figure 2B:
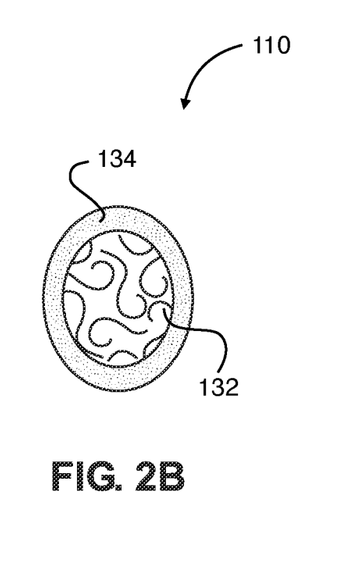
FIG. 2B shows a cross-sectional view of a tourniquet as one aspect of the surgical instrument for occlusion of uterine blood vessels.

With reference to FIG. 2A, in some embodiments, the introducer 120 may define a flat inner surface 128 to accommodate the tourniquet 110. However, in some embodiments, the introducer 120 may define a lengthwise, concave curve or groove to more securely maintain the tourniquet 110 against the inner surface of the introducer 120. The foregoing examples are offered by way of example only and will not limit the invention.

Figure 3:
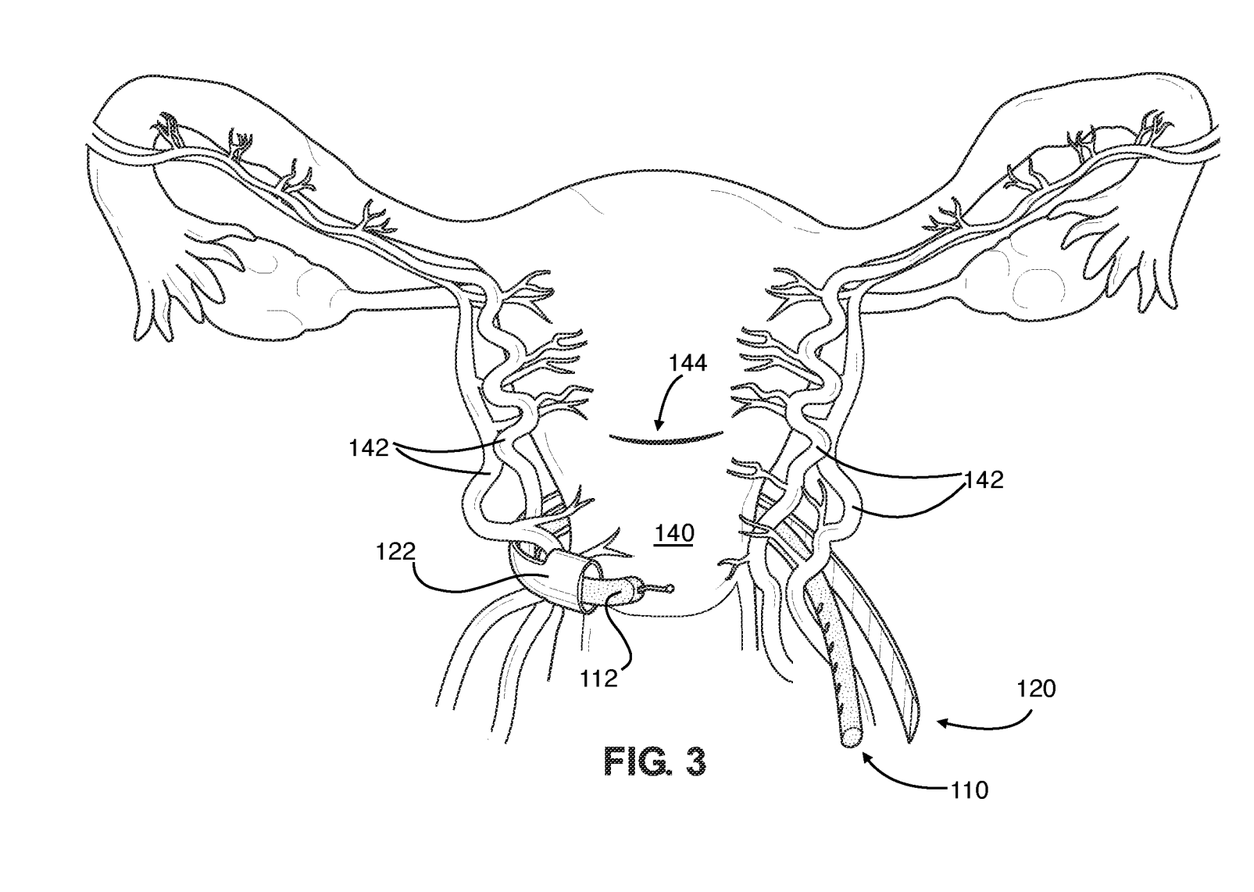
FIG. 3 shows a tourniquet and introducer being placed around a lower uterine segment and uterine vessels in accordance with one embodiment of the invention.
Figure 4:
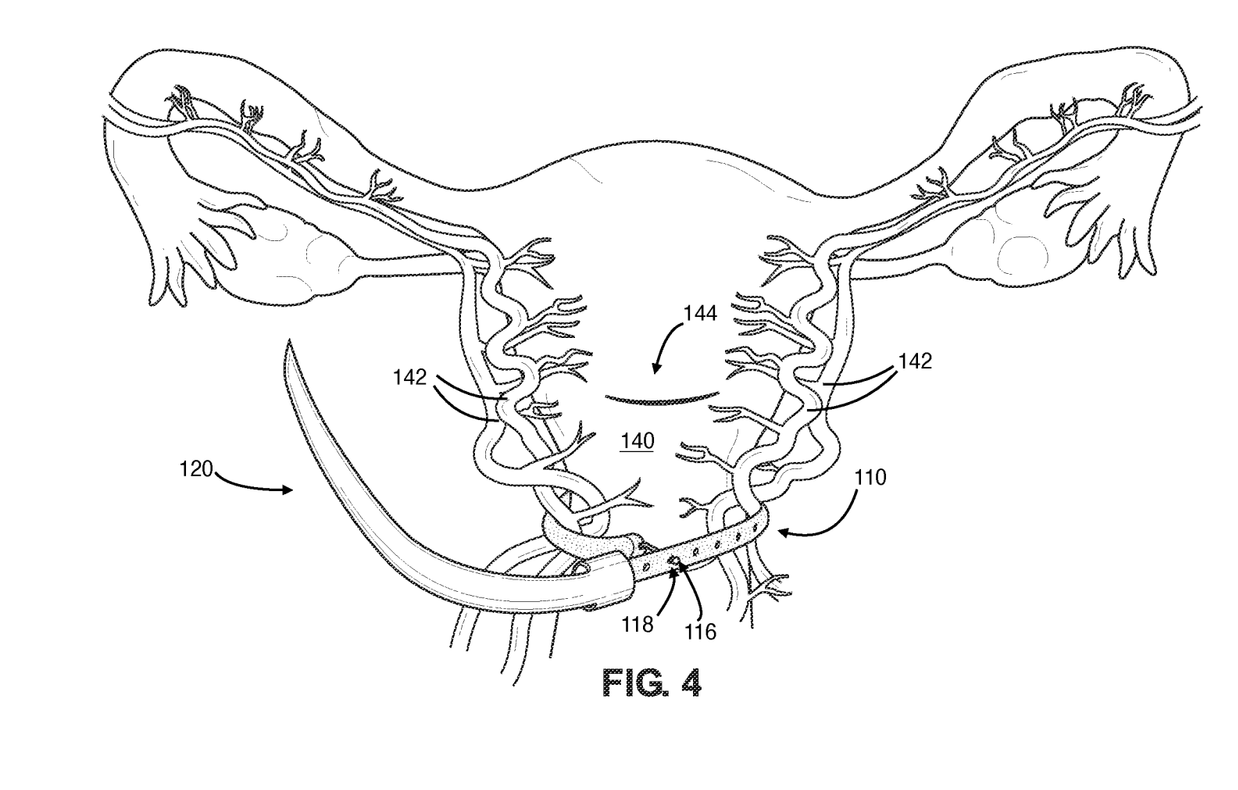
FIG. 4 shows a tourniquet removably secured around a lower uterine segment and uterine vessels, with an introducer being removed from an end of the removably secured tourniquet in accordance with one embodiment of the invention.

FIGS. 3 and 4 show the tourniquet 110 and introducer 120 used in the context of uterine anatomy for the purposes of clarification only and not limitation. That is, it is contemplated that the surgical instrument may be deployed to at least partially occlude blood flow to other body parts and structures without departing from the invention. In some embodiments, introducer 120 is operative to guide the tourniquet 110 into place around a patient's lower uterine segment 140, and any surrounding uterine vessels 142, ligaments (not pictured), and other structures, as desired or needed. In the present example, the tourniquet 110 is applied beneath an incision 144 made in the uterine tissue. Then, with reference in particular to FIG. 4, the tourniquet 110 is secured in a loop beneath such incision 144 when the lashing member 116 is engaged with a selected hole 118 in the tourniquet 110. The introducer 120 may be slidably adjusted along the length of the tourniquet 110 to permit engagement of the lashing member 116 and hole 118.

In practice, the introducer 120 provides the flexible and resilient tourniquet 110 with a pathway around tissue, ligaments, and/or vessels near a surgical site, which, in the exemplary embodiment, would be the incision 144 in the uterus.

Figure 5:
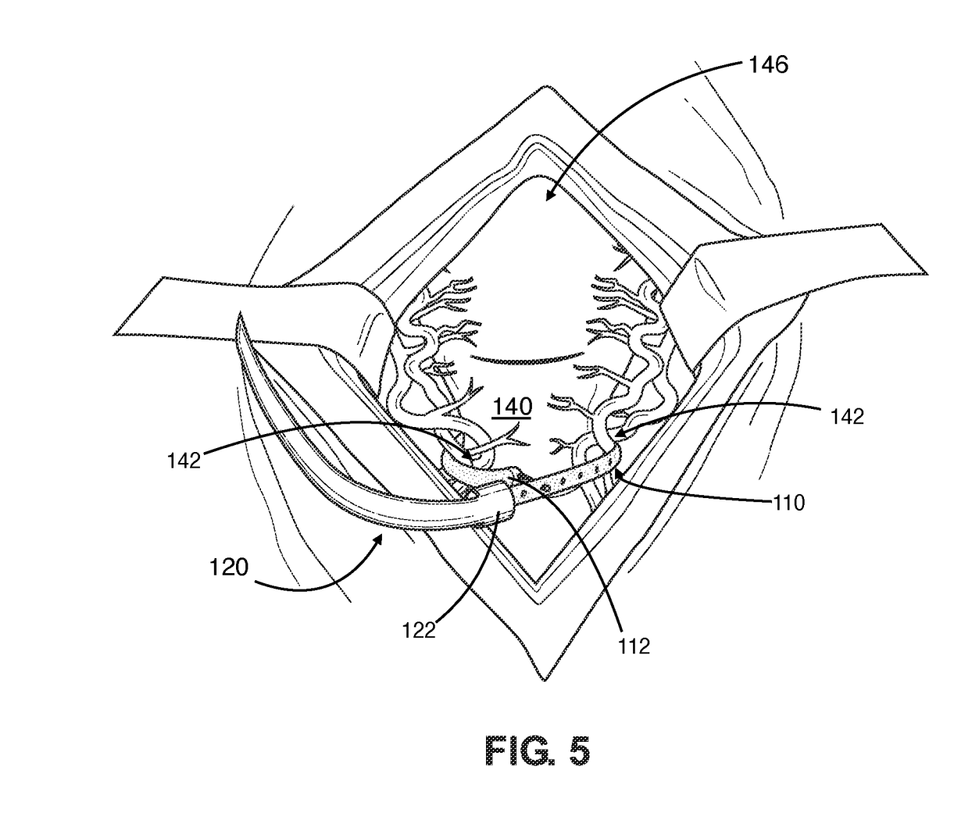
FIG. 5 illustrates a tourniquet removably secured around a lower uterine segment and uterine vessels within an incised abdomen, with an introducer being moved from an end of the removably secured tourniquet in accordance with one embodiment of the invention.

With reference to FIGS. 3-5, and as noted above, the introducer 120 may be generally resistant to deformation but is not completely inflexible. Indeed, this avoids a need to handily manipulate nearby but ultimately uninvolved structures as well. For instance, a patient's bladder and other structures, such as ureters, (not shown) may be positioned in front of or proximate to the patient's lower uterine segment, ligaments, and/or vessels. Thus application of a tourniquet around the lower uterine segment 140, uterine vessels 142, and/or uterine ligaments (not shown) within a retracted abdomen, in the absence of an introducer may require potentially injurious manipulation of the bladder, ureters, and other anatomical structures. When deployed during a surgical procedure on the uterus, however, the first end 122 of the introducer 120 as well as the sheathed first end 112 of the tourniquet 110 may be threaded behind or along a back side of the lower segment 140 of the uterus, uterine ligament (s), and/or uterine vessel(s)—avoiding disturbance of the bladder (not shown) and other structures as needed. Then, from a front side of the lower segment 140 of the uterus, the introducer 120 may be slidably adjusted toward the second end 114 of the tourniquet 110 to permit insertion of the lashing member 116 into one of the plurality of holes 118 in order to form the tourniquet 110 as a secure loop around the lower segment 140 of the uterus, uterine ligaments, and/or uterine vessels 142. The introducer 110 may be sliadably removed from the tourniquet 110 once the tourniquet 110 is secured as a loop around the lower segment 140 of the uterus, uterine ligaments, and/or uterine vessels 142 to the desired degree, or once the first end 112 of the tourniquet 110 is accessible from the front side of the lower segment 140 of the uterus, as desired by a user.

Figure 6:
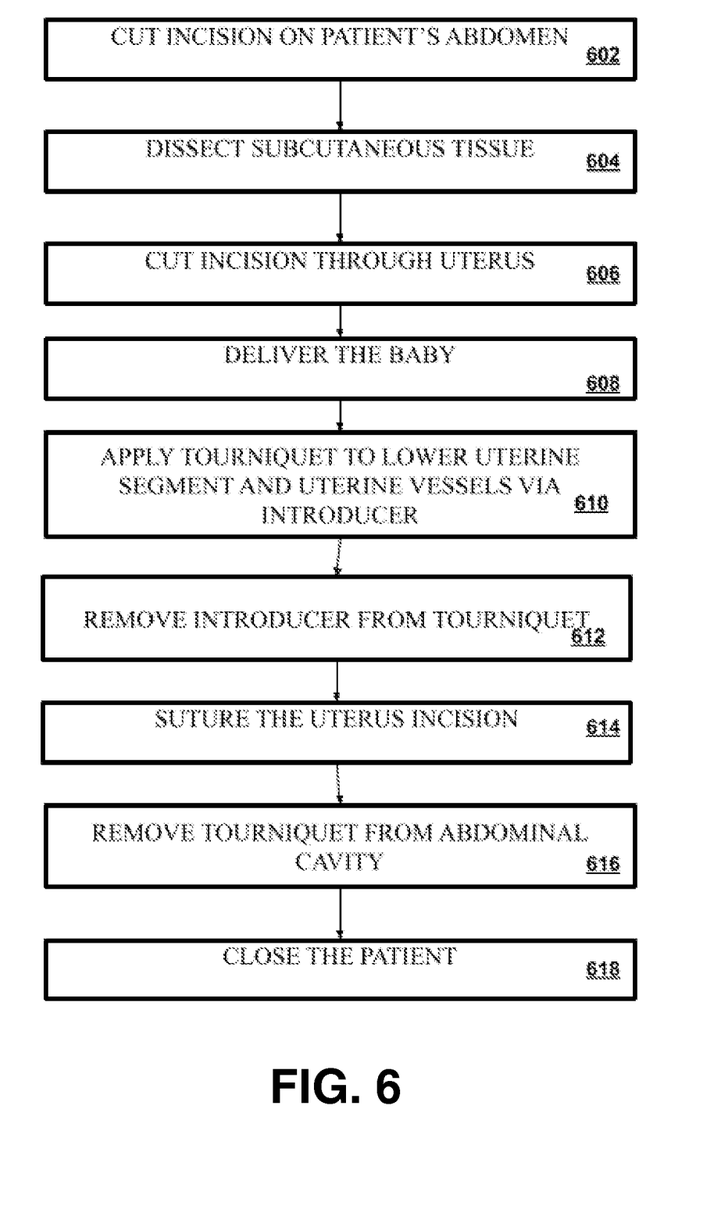
FIG. 6 shows a flowchart illustrating a method for performing a C-section in accordance with one embodiment of the invention.

With reference to FIG. 6, a method for performing a C-section may include the steps of cutting an incision on the patient's abdomen (block 602); dissecting through one or more layers of subcutaneous tissue to expose the uterus (block 604); cutting an incision through the uterus (block 606); delivering a baby from the uterus (block 608); delivering a placenta from the uterus (block 610); applying pressure to one or more uterine vessels by a surgical instrument around a lower segment of the uterus and such one or more uterine vessels (block 610); removing the introducer from the tourniquet (block 612); suturing the incision through the uterus (block 614); removing the tourniquet from the abdominal cavity (block 616) such as by releasing the lashing member from the selected hole on the tourniquet; and closing the patient (block 618). In particular, and as described above, applying pressure to the one or more uterine vessels comprises threading the first end of the tourniquet around a back side of the lower segment of the uterus and the one or more uterine vessels and, from a front side of the lower segment of the uterus, inserting the lashing member into one of the plurality of holes in order to form the tourniquet as a secure loop around the lower segment of the uterus and the one or more uterine vessels.

It is notable that in order to clamp the uterine vessels with ordinary surgical instruments, it may be necessary to physically expose such vessels and the lower uterine segment. Using the tourniquet and introducer under the disclosure may avoid a need to do so and thus avoid potential injury by undue manipulation of the compromised or otherwise vulnerable organs. This is because the relatively low profile of the introducer enables placement of the tourniquet around the lower uterine segment and vessels broadly and requires less precise application than alternative proposals do.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the surgical instrument and method for occlusion of uterine blood vessels with which that terminology is associated. In general, the terms used in the following claims should not be constructed to limit the surgical instrument and method for occlusion of uterine blood vessels to the specific embodiments disclosed in the specification unless the above description section explicitly define such terms. Accordingly, the actual scope encompasses not only the disclosed embodiments, but also all equivalent ways of practicing or implementing the disclosed system, method and apparatus. The above description of embodiments of the surgical instrument and method for occlusion of uterine blood vessels is not intended to be exhaustive or limited to the precise form disclosed above or to a particular field of usage.

While specific embodiments of, and examples for, the method, system, and apparatus are described above for illustrative purposes, various equivalent modifications are possible for which those skilled in the relevant art will recognize.

While certain aspects of the method and system disclosed are presented below in particular claim forms, various aspects of the method, system, and apparatus are contemplated in any number of claim forms. Thus, the inventor reserves the right to add additional claims after filing the application to pursue such additional claim forms for other aspects of the surgical instrument and method for occlusion of uterine blood vessels.

What is claimed is:

1. A surgical instrument for at least partial occlusion of uterine blood vessels in a lower uterine segment, comprising;
   an elongated, flexible, and resilient tourniquet in any form selected from the group consisting of a band, strip, tape, cord, and belt, the tourniquet having a first end and second end;
   a lashing member disposed at or proximate to the first end; and
   an introducer configured as a curved length of material sized to receive the tourniquet thereon and operative to guide the first end of the tourniquet around the lower uterine segment;
   wherein a portion of the tourniquet proximate to the second end defines a plurality of holes configured to selectively and securely yet releasably receive the lashing member to form the tourniquet as a loop.

2. The surgical instrument of claim 1, wherein the tourniquet is compressible.

3. The surgical instrument of claim 1, wherein the tourniquet comprises a plurality of layers, and an inner layer of the tourniquet is selected from the group consisting of surgical foam and gel.

4. The surgical instrument of claim 1, wherein the tourniquet comprises a plurality of layers, and an inner layer of the tourniquet is an outer layer selected from the group consisting of surgical cotton and gauze.

5. The surgical instrument of claim 1, wherein the introducer has a first end defining a channel configured to removably receive the tourniquet therethrough and a second end defining an elongated handle.

6. The surgical instrument of claim 1, wherein the tourniquet is up to about 20 inches long and up to about 1 inch wide.

7. The surgical instrument of claim 1, wherein the tourniquet defines an inside and an outside, the outside defining a convex curve and the inside defining a flat surface,
   wherein the inside is configured to physically contact targeted uterine tissue when in use.

8. A method for performing a cesarean section comprising the steps of:
   a) cutting an incision on the patient's abdomen;
   b) dissecting through one or more layers of subcutaneous tissue to expose the uterus;
   c) cutting an incision through the uterus;
   d) delivering a baby from the uterus;
   e) delivering a placenta from the uterus;
   f) applying pressure to one or more uterine vessels by a surgical instrument around a lower segment of the uterus and such one or more uterine vessels, the surgical instrument comprising:
      an elongated, flexible, and resilient tourniquet having a first end and second end, a portion of the tourniquet proximate to the second end defining a plurality of holes configured to securely yet releasably engage a lashing member disposed at or proximate to the first end of the tourniquet;

g) suturing the incision through the uterus;

h) releasing the lashing member from the selected hole on the tourniquet;

i) removing the tourniquet from the abdominal cavity; and j) closing the patient;

wherein applying pressure to the one or more uterine vessels comprises threading the first end of the tourniquet around a back side of the lower segment of the uterus and the one or more uterine vessels and, from a front side of the lower segment of the uterus, inserting the lashing member into one of the plurality of holes in order to form the tourniquet as a secure loop around the lower segment of the uterus and the one or more uterine vessels.

9. The method of claim 8, wherein the surgical instrument further comprises an introducer configured as a curved sheath sized to removably receive the tourniquet therethrough and operative to guide the first end of the tourniquet around the lower segment of the uterus when threading the first end of the tourniquet around the back side of the lower segment of the uterus and the one or more uterine vessels.

10. The method of claim 9, further comprising disengaging the introducer from the tourniquet after threading the first end of the tourniquet around the back side of the lower segment of the uterus and the one or more uterine vessels but before inserting the lashing member into one of the plurality of holes.

11. The method of claim 8, wherein the tourniquet comprises a plurality of layers, and a compressible inner layer is selected from the group consisting of compressible surgical foam and gel.

12. The method of claim 8, wherein the tourniquet comprises a plurality of layers, and an outer layer is selected from the group consisting of surgical cotton and gauze.

13. The method of claim 8, wherein the tourniquet defines an inside and an outside, the outside defining a convex curve and the inside defining a flat surface, wherein at least a portion of the flat inner surface of the tourniquet maintains physical contact against the one or more uterine vessels when the tourniquet is formed as a secure loop around the lower segment of the uterus and the one or more uterine vessels.

14. A surgical instrument for at least partial occlusion of uterine blood vessels, comprising:

a tourniquet defined by any of an elongated, flexible, and resilient tourniquet in any form selected from the group consisting of a band, strip, tape, cord, and belt, the tourniquet having a first end and second end; and a lashing member disposed at or proximate to the first end;

wherein a portion of the tourniquet proximate to the second end defines a plurality of holes configured to securely yet releasably receive the lashing member to form the tourniquet as a loop.

15. The surgical instrument of claim 14, further comprising an introducer configured as a curved sheath sized to removably receive the tourniquet therethrough and operative to guide the first end of the tourniquet around the lower uterine segment, wherein the introducer has a first end defining a channel configured to removably receive the tourniquet therethrough and a second end defining an elongated handle.

16. The surgical instrument of claim 15, wherein the tourniquet is compressible.

17. The surgical instrument of claim 15, wherein the tourniquet comprises at least an inner layer and an outer layer, wherein the inner layer is selected from the group consisting of surgical foam and gel, and the outer layer is selected from the group consisting of surgical cotton and gauze.

18. The surgical instrument of claim 15, wherein the tourniquet is up to about 20 inches long and up to about 1 inch wide.

19. The surgical instrument of claim 15, wherein the tourniquet defines an inside and an outside, the outside defining a convex curve and the inside defining a flat surface, wherein the inside is configured to physically contact targeted uterine tissue when in use.

* * * * *